United States Patent
Carter et al.

(12)

(10) Patent No.: US 6,328,932 B1
(45) Date of Patent: Dec. 11, 2001

(54) DEVICES AND METHODS FOR THE DETECTION OF BASIC GASES

(75) Inventors: Michael T. Carter; Michael Schwartz, both of Boulder, CO (US)

(73) Assignee: Eltron Research, Inc., Boulder, CO (US)

(*) Notice: Subject to any disclaimer, the term of this patent is extended or adjusted under 35 U.S.C. 154(b) by 0 days.

(21) Appl. No.: 08/853,380

(22) Filed: May 8, 1997

(51) Int. Cl.[7] .................................................. G01N 21/01

(52) U.S. Cl. ........................ 422/82.06; 422/86; 422/91; 422/82.05; 422/82.09; 436/111; 436/112; 436/164

(58) Field of Search ........................ 422/86, 82.05, 422/82.06, 82.07, 82.08, 82.09, 82.11, 91; 436/111, 112, 172

(56) References Cited

U.S. PATENT DOCUMENTS

| | | | |
|---|---|---|---|
| 3,455,656 | 7/1969 | Roberts et al. | 23/254 |
| 3,575,835 | 4/1971 | Smith et al. | 204/195 |
| 4,200,608 | 4/1980 | Croomes et al. | 422/97 |
| 4,201,634 | 5/1980 | Stetter | 204/1 T |
| 4,394,239 | 7/1983 | Kitzelmann et al. | 204/414 |
| 4,513,087 | 4/1985 | Guiliani et al. | 436/96 |
| 4,560,248 | * 12/1985 | Cramp et al. | 350/96.34 |
| 4,775,633 | 10/1988 | Rounbehler | 436/106 |
| 4,789,638 | 12/1988 | Kramer et al. | 436/111 |
| 4,900,681 | 2/1990 | Taffe et al. | 436/106 |
| 5,173,432 | * 12/1992 | Lefkowitz et al. | 436/138 |
| 5,212,099 | * 5/1993 | Marcus et al. | 436/172 |
| 5,308,771 | * 5/1994 | Zhou et al. | 436/39 |
| 5,372,784 | * 12/1994 | Morris et al. | 422/82.08 |
| 5,405,583 | * 4/1995 | Goswami et al. | 422/86 |
| 5,610,393 | * 3/1997 | Klimcak et al. | 250/227.14 |
| 5,637,507 | * 6/1997 | Wicks et al. | 436/166 |

OTHER PUBLICATIONS

Ayyangar, N. R and Tilak, B. D. in "The Chemistry of Synthetic Dyes", vol. IV, Chapter III, "Basic Dyes", K. Venkataraman (ed.), Academic Press, New York and London, pp. 103–160, 1971.*

Ayyangar, N. R. and Tilak, B. D. (1971) in *The Chemistry of Synthetic Dyes*, vol. IV, Chapter III, "Basic Dyes," K. Venkataraman, (ed.), Academic Press, New York and London, pp. 103–160.

Collins, G. E. and Rose–Pehrsson, S. (1994), "The Fluorescent Detection of Hydrazine, Monomethylhydrazine, and 1,1–Dimethylhydrazine by Derivatization with Aromatic Dicarboxaldehydes," DTIC Report Bibliography, Search Control No. SBT040, Ad–A288 877, Dept. of the Navy, Washington, D.C., p. 8.

Collins, G. E. et al. (1995), "Chemiluminescence Detection of Hydrazine Vapor," Talanta 42(4):543–551.

(List continued on next page.)

Primary Examiner—Jill Warden
Assistant Examiner—Dwayne K Handy
(74) Attorney, Agent, or Firm—Greenlee, Winner and Sullivan, P.C.

(57) ABSTRACT

This invention provides a fiber optic sensor and sensor devices for the reversible detection of basic gas analytes, including hydrazine, alkyl hydrazines, amines, ammonia, and related chemical species. The optical fiber sensor is formed in an optical fiber which conventionally comprises an optical fiber core and a cladding layer. Transducer molecules are immobilized in contact with an exposed surface of the fiber core to allow interaction of the immobilized species with analytes in the environment around the sensor. Preferred transducer molecules for detection of basic gases, particularly hydrazine and hydrazine derivatives, are xanthene dyes and triphenylmethane dyes, including malachite green and crystal violet. The sensors of this invention can be employed in a variety of device configurations including single-site sensors and multiple-site sensor networks.

44 Claims, 7 Drawing Sheets

OTHER PUBLICATIONS

Eiceman, G. A. et al. (1993), "Ion Mobility Spectrometry of Hydrazine, Monomethylhydrazine, and Ammonia in Air with 5–Nonanone Reagent Gas," Anal. Chem. 65:1696–1702.

Ellis, D. L. et al. (1996), "Conductive Polymer Films as Ultrasensitive Chemical Sensors for Hydrazine and Monomethylhydrazine Vapor," Anal. Chem. 68:817–822.

Klimcak, C. et al., "Development of a Fiber Optic Chemical Dosimeter Network for Use in the Remote Detection of Hydrazine Propellant Vapor Leaks at Cape Canaveral Air Force Station," SPIE 2293:209–219.

Klimcak, C. et al., "A Remote Fiber Optic Dosimeter Network for Detecting Hydrazine Vapor," SPIE 2367:80–88.

Venkataraman, K. (ed.) (1952) in *The Chemistry of Synthetic Dyes*, Chapter XXIII, "Diphenylmethanes and Triphenylmethanes," Academic Press, Inc., Publishers, New York, pp. 705–735.

Ratcliffe, N. M. (1990), "Polypyrrole–based sensor for hydrazine and ammonia," Anal. Chim. Acta 239:257–262.

Stetter, J. R. et al. (1978), "The Electrochemical Oxidation of Hydrazine and Methylhydrazine on Gold: Application to Gas Monitoring," J. Electochem. Soc.: Electrochem. Sci and Technol. 125(11):1804–1807.

Stetter, J. R et al. (1979), "Electrochemical Determination of Hydrazine and Methyl– and 1,1–Dimethylhydrazine in Air," Talanta 26:799–804.

Stetter, J. R. et al. (1991), "Modulated Photoionization Detection of Hydrazine Compounds in Mixtures without Prior Separation," Anal. Chem. 63:1755–1759.

Vartanyan, A. T. (1961), "The Reversible Bleaching of Solid Layers of Triphenylmethane Dyes in Hydrazine Vapour," Russ. J. Phys. Chem. 35(10):1105–1109.

Vartanyan, A. T. (1962), "A Spectroscopic Investigation of Interaction Between Hydrazine and Neutral Dyes with Phenolic Hydroxy–Groups," Russ. J. Phys. Chem. 36(10):1142–1145.

Vartanyan, A. T. (1962), "Reversible Bleaching of Solid Layers of Xanthene Dyes in Hydrazine Vapour," Russ. J. Phys. Chem. 36(9): 1021–1024.

* cited by examiner

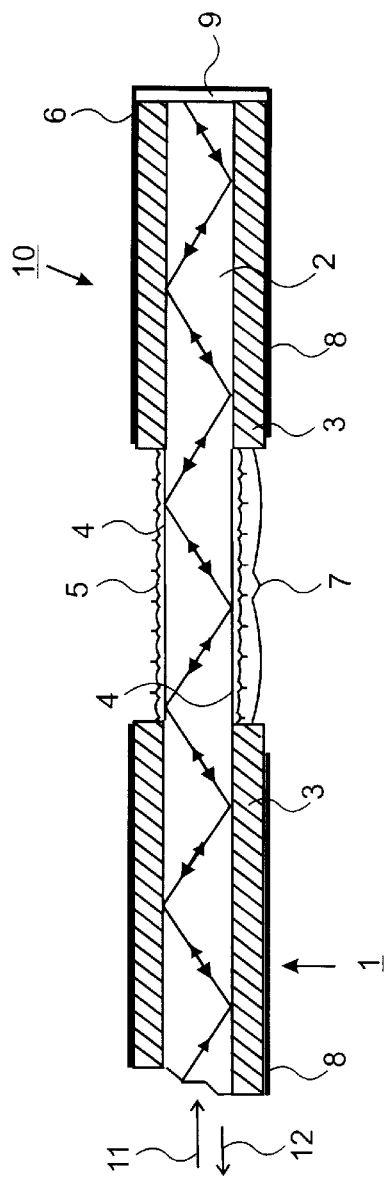
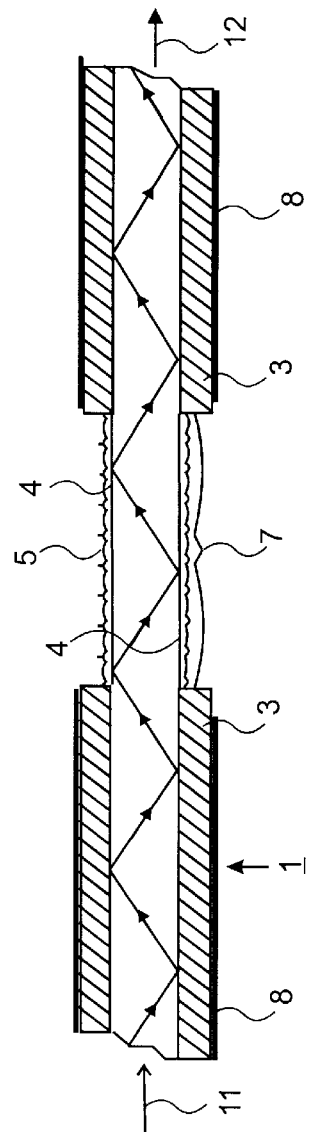
FIG. 1A
FIG. 1B

DEVICES AND METHODS FOR THE DETECTION OF BASIC GASES

This invention was made with sponsorship from the United States Air Force Phillips Laboratory at Kirtland AFB, NM, with funding from the Small Business Innovative Research Program under contract F29601-96-C0024. The USAF technical oversight has been provided by the Space and Missile Systems Center (SMC/CLME) at Los Angeles AFB, CA.

FIELD OF THE INVENTION

This invention relates to the reversible detection and measurement of trace amounts of basic gases, and particularly to the detection of hydrazine and alkyl hydrazines. More specifically the invention relates to a fiber optic sensor comprising dyes which change color and/or bleach on interaction with a basic gas.

BACKGROUND OF THE INVENTION

Several types of gas sensors, including electrochemical, surface acoustic wave (SAW), thermal conductivity and fiber optic sensors, are known in the art. As a class, fiber optic sensors have significant potential advantage over other sensing techniques. Their small size (3–1000 $\mu$M) permits in-situ sensing; long-term stability can likely be achieved using silica or plastic fibers; remote sensing using a fiber optic network in which a fiber carries the signal to a central detector is possible; manufacturing and maintenance costs are low when standard optoelectronic components are utilized; the sensors, themselves, are non-electrical devices which may alleviate safety concerns; the sensors can be incorporated into a multi-site network; and the sensors are versatile, since the optical sensing method can use absorption (including reflectance and scattering), emission, or refractive index changes for detection; and it is possible in these optical methods to use different light frequencies.

SUMMARY OF THE INVENTION

This invention provides a fiber optic sensor and sensor devices for the reversible detection of basic gas analytes, including hydrazine, alkyl hydrazines, amines, ammonia, and related chemical species. The optical fiber sensor is formed in an optical fiber which conventionally comprises an optical fiber core and a cladding layer. Transducer molecules are immobilized in contact with an exposed surface of the fiber core to allow interaction of the immobilized species with analytes in the environment around the sensor. The transducer molecule undergoes a change in optical response, e.g., a color change, a change in fluorescence or a change in another measurable optical response, on interaction with the analyte. An optical property of light input into the optical fiber is affected by the change in optical response of the immobilized transducer molecules interacting with the analyte. The change in the optical property of light is detected and measured to detect the presence of the analyte and to measure the amount of analyte present in the environment of the sensor.

The transducer molecule is preferably a dye which undergoes a color change on interaction with the analyte. The dye is preferably selected from the group consisting of triphenylmethane dyes and xanthene dyes or combinations thereof, particularly those dyes which undergo a reversible color change, including bleaching, on interaction with the analyte. The transducer molecule is present, immobilized in contact with the optical fiber core, in an amount sufficient to allow detection of the analyte by the sensor.

Preferred transducer molecules for detection of basic gases, particularly hydrazine and hydrazine derivatives, are triphenylmethane dyes, with malachite green and crystal violet being more preferred.

In specific embodiments, the transducer molecule is a dye immobilized in a polymer layer in contact with the fiber core. A preferred polymer is poly(vinylchloride). The polymer layer is preferably a thin layer, several $\mu$m up to about 10 $\mu$m thick. The polymer material is preferably plasticized (i.e., the layer contains a plasticizer) and the preferred plasticizer for poly(vinylchloride) is a dialkyl sebacate plasticizer and more preferably the plasticizer for poly (vinylchloride) is bis-(2-ethylhexyl)sebacate.

The fiber optic sensor of this invention can be configured in several different modes.

The sensor, in any sensing mode or configuration, is optically coupled to a light source (signal light source) which provides input light having at least one wavelength (or band of wavelengths) at which a change in optical response due to the interaction of the analyte with the transducer molecule can be monitored (herein the signal wavelength). The sensor is also optically coupled to a detector, e.g., a photodetector, to allow measurement of optical changes, e.g., light intensity, or fluorescence intensity, of light exiting the sensor.

In any sensing mode or configuration, the sensor can be provided with a reference system to compensate for variations in optical response unrelated to the presence of analyte, e.g., light source and detector variation. The sensor can be equipped with a reference light source optically coupled to the sensor to provide a second wavelength of light (or band of wavelengths) that is substantially unaffected by the interaction of the transducer with the analyte. A single light source providing light at both the reference and signal wavelengths can also be used. Light exiting the sensor at the signal wavelength and at reference wavelength are independently detected for comparison. A single detector can be used to measure both the reference and signal wavelength. The sensor is optionally equipped with a second reference detector provided to detect light at the reference wavelength.

The sensors of this invention can be employed in a variety of device configurations including single-site sensors and multiple-site sensor networks. In the multi-site device mode, several sensors, typically spatially separated, can be monitored for the presence of a basic gas to determine its concentration.

The invention also provides a method for detection of basic gases, including hydrazine and hydrazine derivatives, using the sensors and sensor devices and networks of this invention. The devices of this invention, particularly those using triphenylmethane dyes as the transducers molecules, are useful for the detection of hydrazines and alkyl hydrazines in the presence of potentially interfering species, such as ammonia.

BRIEF DESCRIPTION OF THE DRAWINGS

FIGS. 1A and 1B are illustrations of a sensor of this invention in a reflection-mode configuration.

DETAILED DESCRIPTION OF THE INVENTION

Figure 2:
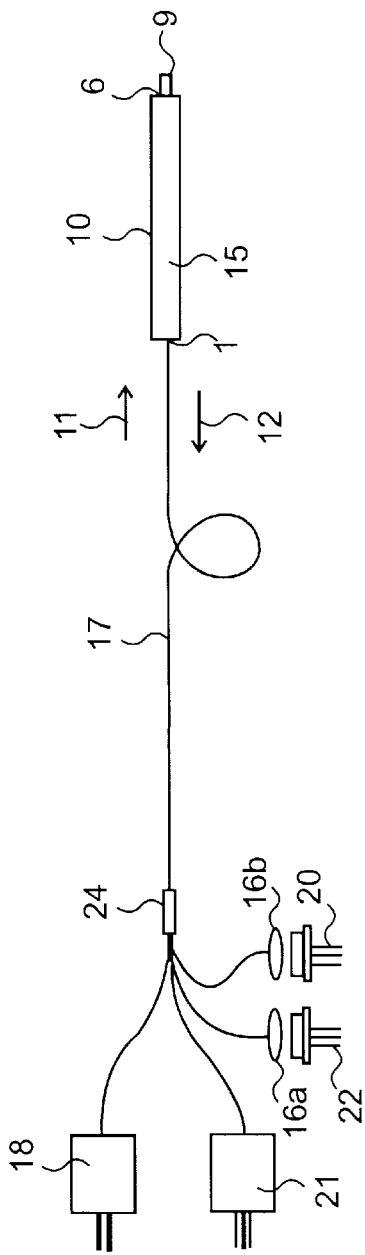
FIG. 2 is an illustration of a single site monitor sensor device of this invention employing a sensor of FIG. 1.

Optical chemical sensor devices of this invention have the same basic components: a light source, a light detector, and a transducer molecule. Most generally, an optical property of the transducer molecule changes on interaction with the species (analyte) to be detected. Light from the light source interacts with the transducer molecule and any change in the optical properties of the transducer induced by its interaction with the analyte are measured at the light detector. In a fiber optic sensor, an optical fiber mediates interaction of light with the transducer molecule and thereafter couples light with the detector.

A transducer molecule used in a fiber optic sensor preferably has several additional properties:

(1) the interaction between the analyte and the transducer molecule that leads to the change in optical properties is preferably reversible to ensure that the sensor can be reused, for example, to allow analyte detection as a function of time;

(2) the interaction between the analyte is preferably fast and the optical property of the sensor preferably rapidly changes with changes in analyte concentration, i.e., sensor response time is fast;

(3) the transducer molecule is preferably chemically and photochemically stable in the environment in which it will be deployed, having long-term stability during operation.

The present invention uses xanthene or triphenylmethane dyes as transducer molecules in coatings on optical fibers to detect basic gases, including hydrazine and alkyl hydrazines, amines and ammonia.

Sensors of this invention can be employed in several different sensing modes and in transmission-mode, scattering-mode, and/or reflection-mode configurations. The sensors, for example, can directly monitor changes in absorption or another optical property of light passing through a layer containing the immobilized transducer molecule. In a transmission configuration of this absorption-sensing mode, light input into the fiber passes through a layer containing immobilized transducer molecules positioned for example, on an exposed end of the optical fiber, exits the exposed fiber end and is coupled into a detector.

In a scattering-mode configuration, light introduced into the entrance end of a fiber at least in part scatters off a transducer molecule layer at an exposed distal end of the fiber, and scattered light travels back along the fiber and is coupled into a detector via the entrance end of the fiber. In an exemplary scattering-sensing mode configuration, also designated an optrode, the transducer molecule is, for example, coated on the distal tip of a fiber optic. The fiber optic carries light from a light source to the distal tip, where it interacts with the transducer molecule/analyte adduct and then is scattered back to the detector.

The fiber optic sensor of this invention is preferably configured in evanescent wave mode in which the immobilized transducer molecule is in contact with the fiber core at its circumference. In this mode, the evanescent wave generated by light traversing the optical fiber interacts with the immobilized transducer molecule. For example, a portion of the fiber cladding is removed exposing a portion of the outer surface of the fiber optic core and transducer molecules are immobilized in contact with the exposed outer surface of the core. For example, a transducer molecule-containing layer is created at the core surface along a portion of the longitudinal axis of the fiber optic. In a transmission configuration of this evanescent-wave-sensing mode, light input into the fiber traverses the fiber and is confined therein by total internal reflection. The evanescent wave of that light (a small portion of the light propagating down the fiber) interacts with immobilized transducer and any analyte and the light ultimately exits the sensor at the distal end of the fiber for coupling to a detector. In a reflection configuration of this evanescent-wave-sensing mode, light introduced into the entrance end of the fiber traverses the fiber and is reflected back along the fiber by a reflective surface at the distal end of the fiber to exit at the entrance end of the fiber for coupling to a detector. In this case, the evanescent wave makes two passes along the fiber interacting with the immobilized transducer molecule layer.

Sensors and sensor devices of this invention are illustrated in FIGS. 1A, 1B-4, wherein the same numbers are used to indicate like features.

Figure 3:
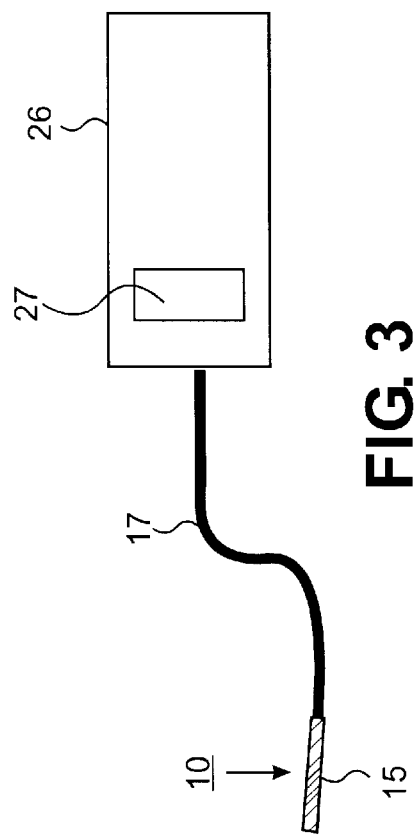
FIG. 3 is an illustration of one mode of application of the sensor device of FIGS. 1 and 2. In this case the sensor is adapted in a hand-held device.
Figure 4:
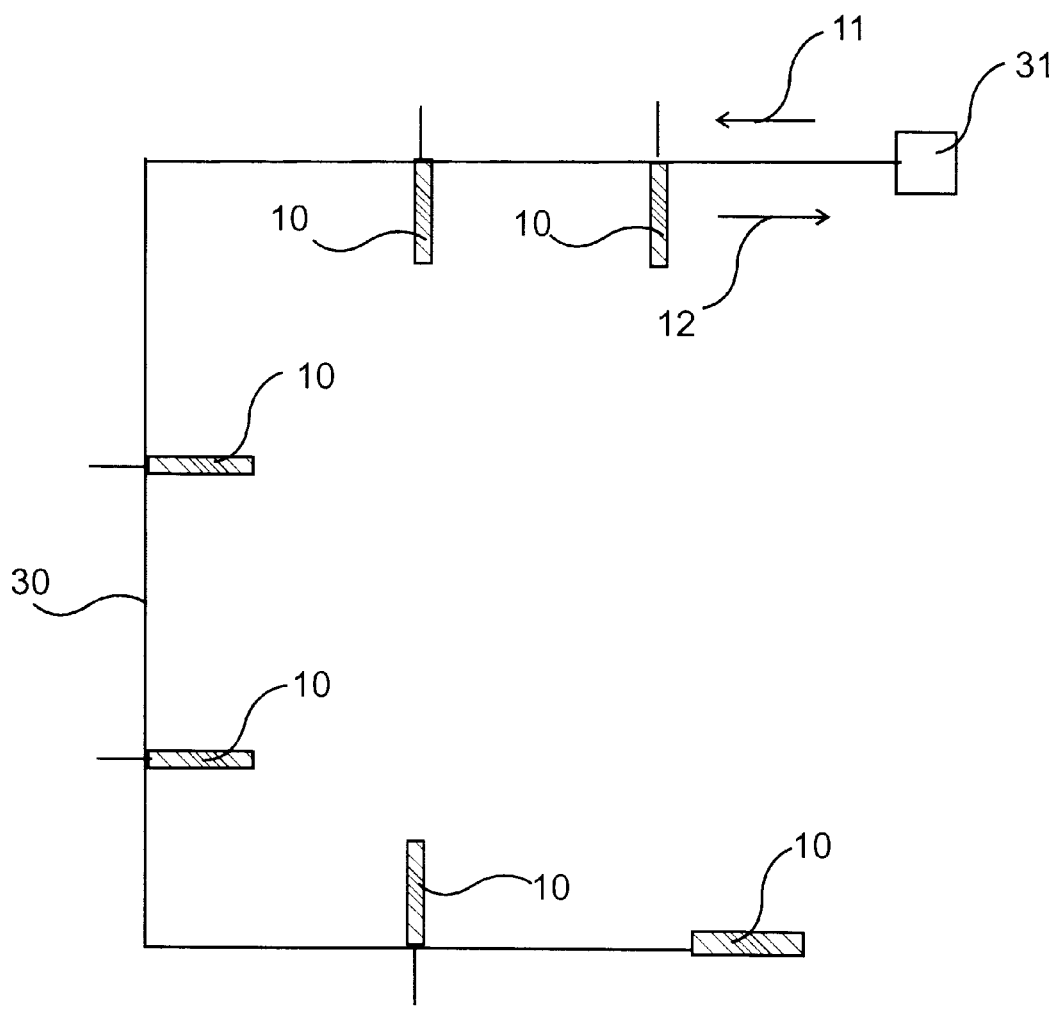
FIG. 4 is illustration of a multiple-site sensor system of this invention.

FIGS. 1A and 1B illustrate detailed views of exemplary sensor configurations of this invention. FIG. 1A is a reflection-mode configuration and FIG. 1B is a transmission-mode configuration. FIG. 2 is a schematic drawing of a single site monitor sensor device of this invention in a reflection-mode configuration. This type of sensor device configuration can, for example, be constructed as a portable instrument, for example in a hand-held instrument as illustrated in FIG. 3. Alternatively, sensors of FIG. 1 can be deployed in a multiple site system as illustrated in FIG. 4.

Evanescent-wave sensors 10 of this invention are illustrated in FIGS. 1A and 1B. In both cases, the sensor is formed on an optical fiber 1 with core 2. In the reflection-mode configuration of FIG. 1A, the sensor is near a distal end 6 of the fiber which carries a reflective coating 9. A portion of the fiber cladding 3, is removed exposing an outer surface 4 of the core of the fiber and a layer 5 comprising the transducer molecule is placed in contact with the core 2 of the fiber at the outer surface 4. The evanescent region is indicated as 7. The fiber may have an outer opaque jacket 8. Light is input into the fiber (as indicated 11) from a source (not shown), input light traverses the optical fiber by total internal reflection and the evanescent wave associated with light traversing the optical fiber can interact with the species in layer 5 to bring about a change in optical response. In the illustrated configuration, light is reflected back, interacting a second time with layer 5, through fiber (exiting as indicated 12) and coupled to a detector (not shown).

In the transmission-mode sensor of FIG. 1B, a portion of the fiber cladding 3, is removed exposing an outer surface 4 of the core of the fiber and a layer 5 comprising the transducer molecule is placed in contact with the core 2 of the fiber at the outer surface 4. The evanescent region is indicated as 7. The fiber may have an outer opaque jacket 8. Light is input into the fiber 11 from a source (not shown), input light traverses the optical fiber by total internal reflection and the evanescent wave associated with light traversing the optical fiber interacts with the species in layer 5. In the illustrated configuration, light is transmitted through the fiber to exit at the fiber end distal to the end through which light entered the sensor. Light exiting the fiber after interaction with layer 5 is coupled into a detector.

More specifically, a transducer molecule, such as of the dyes discussed herein, is formed into a layer (for example, by thermal or solvent deposition or by direct chemical attachment of the transducer to the fiber surface) or introduced into a layer (for example, by doping into a layer-forming material) of polymer or plastic or other chemically and optically inert carrier. The layer must permit penetration of the analyte to be detected (i.e., hydrazine, hydrazine derivative or other basic molecule) to allow interaction with the transducer dye. The dye is chosen as discussed below to give a significant change in color or bleaching on interaction with hydrazine or other basic molecules. Preferably the color change or bleaching is reversible so that the sensor is reusable, rapid, sensitive to analyte concentration and allows real-time, continuous monitoring of analyte.

The sensor device of FIG. 2 has a fiber optic sensor 10, with sensor enclosure 15, near the distal end 6 of an optical fiber 1 that is optically coupled through the optical fiber (optical cable 17) to a signal light source 18 which provides at least one wavelength (a signal wavelength or wavelengths) of light that is affected by interaction of hydrazine (or other basic molecule) with the transducer molecule in layer 5. Light is input 11 into the sensor 10. Optical fiber end 6 has a reflective surface 9 to reflect light from the light source back along the optical fiber to detector 20. The photodetector is selected to detect the change in optical signal, which in this configuration is reflected back through the fiber, from the detection source after traversing the sensor region. The sensor device optionally has a second reference light source 21 which provides at least one wavelength (a reference wavelength or wavelengths) of light that is not affected by the interaction of analyte with the transducer molecule in layer 5. The detector may be selected to simultaneously or sequentially monitor the optical signal reflected back from the sensor of both the detection and reference source. Alternatively, the sensor device can have an optional second detector 22, so that there is one detector for the detection source (and its wavelength) and one for the reference source (and its wavelength).

As illustrated in FIG. 2, light from the source(s) (18 and optionally 21), is coupled into the optical fiber and light exiting the sensor is coupled into the detector(s) (20 and optionally 22) using conventional fiber optic couplers or splitters. A 1×4 coupler 24 is illustrated. Optionally, each of the signal detector and reference detector can be optically coupled to the light exiting (12) the sensor through wavelength filters (16a and 16b, respectively) which each pass a selected wavelength range. The signal filter 16a is selected to exclude wavelengths from the reference light source (or at least the reference wavelength) and preferably to pass a relatively narrow band of wavelengths around the signal wavelength into detector 20. The reference filter 16b is selected to exclude wavelengths from the detection light source 18 (or at least the signal wavelength) and preferably to pass a relatively narrow band of wavelengths around the reference wavelength into detector 22. If the detection and reference light sources (18 and 21, respectively) are alternately pulsed (18 on when 21 is off and 21 on when 18 is off) the wavelength filters are not required. A single detector for both the reference and signal wavelengths can be used when light sources 18 and 21 are alternately pulsed, if the detector signal is gated to match the pulsing sequence of the sources to allow independent collection of signal and reference data.

The sensor device of FIG. 2 also has an appropriate power supply, optional circuitry for pulsing of the light sources and detection electronics (optionally including circuitry to match source pulsing to data collection) as well as optional computer analysis (not shown).

FIG. 3 is an illustration of one mode of application of the sensor device of FIGS. 1 and 2. An optical fiber cable 17 optically couples the fiber optic sensor 10 (inside of protecting cover 15). In the hand-held device illustrated, the cable can be up to several meters in length. Cover 15 is provided to protect the transducer molecule layer on the bare fiber. The cover is preferably inert, does not interfere with the interaction of the transducer with the analyte and allows access of analyte to the immobilized transducer. The cover can be a porous polymer which allows for diffusion of the gaseous analyte to the sensor. Alternatively, a baffling system can be used which prevents light and particles from coming in contact with the sensor yet allows for analyte to interact with the sensor.

The optoelectronics of the device, (light source(s) and detector(s) and associated electronics and a power supply) are contained in a relatively compact unit 26 small enough for hand-held operation. The photodetector(s), e.g. 20 and 22 of FIG. 2 can be electronically linked via an analog to digital converter to display 27 to provide a visual indication of the amount of analyte present, for example as a concentration measurement. Alternatively, the output of the detector(s) can be electronically linked to an alarm (e.g., a light or sound signal) to indicate the presence of analyte or to indicate that the analyte is present at a concentration level above a chosen threshold.

Sensors of this invention can be successfully employed in environments containing chemical species that potentially interfere with detection of basic gasses, for example, $SO_2$ an acidic species, does not substantially interfere with detection of basic gases using xanthene or triphenylmethane dyes. Measurements of hydrazines, alkyl hydrazines and other hydrazine derivatives by sensors of this invention can be successfully performed in the presence of potential interferents $H_2S$ and ammonia. These sensors are significantly more sensitive to hydrazines than to ammonia. The sensors of this invention are useful for the detection of ammonia, itself. It will be readily apparent that it may be necessary to adjust the signal wavelength in the sensor devices of this invention to minimize interference from changes in optical response due to potential interferent species.

FIG. 4 is a schematic illustration of a multiple sensor site application of the sensors of this invention, in a linear array network architecture. Fiber optic cable 30 links a plurality of sensors 10 (six individual sensors are shown). The sensor network is optically coupled to a monitor 31. Sensors in the network can be spaced throughout the environment that is to be monitored with sensing sites separated by meters or by kilometers. As in the device of FIG. 2, light is reflected back from each sensor (each sensor has a fiber optic end carrying a reflective surface) through the fiber to the monitor for detection. The network monitor houses light source(s), preferably pulsed light sources, optical couplers, detectors, preferably those that can be modulated, as in FIG. 2 and related optics and electronics, including pulsing and timing circuits. The network monitor can be configured to provide a discernible indication (for example, a visual or auditory signal) of the presence and/or the concentration of analyte at a given sensor site in the network.

Detection in a multi-site network of FIG. 4 is done in a manner that allows changes in optical response from different sensors to be independently detected and a given optical response to be linked to a given sensor. A fiber optic network of sensors requires some form of multiplexing (See: R. Kist (1989) in "Optical Fiber Sensors: Systems and Applications," Vol. II (Culshaw, B and Dakin, J., eds.) ArtechHouse, MA, Ch. 1.).

Time division multiplexing (TDM), as discussed in more detail in the examples, is one convenient way to implement multiplexing that will provide spatial resolution on the order of several meters (between sensors sites). Briefly, TDM is implemented by pulsing the light source (at time T) and following light intensity at the detector as a function of time $(T+D_n)$, where $D_n$ is the delay time from the light pulse for light to be reflected back from sensor n. Signal reflected back from each spatially separate, fixed sensor site is detected as a function of time. Delay time represents distance from the detector and identifies the sensor location. Data for a given sensor is collected in the appropriate time window for its reflection back from the sensor.

The use of a reference system, as discussed above, can be implemented in the multi-site system, for example, by providing alternating pulses of reference and signal wavelength to the network, combined with appropriate time-dependent data collection. Signal and any reference data can be digitized, stored and compared to provide desired visual or auditory output detecting the presence of analyte or quantitating the amount of analyte present at each sensor site.

When a sensor network is operated using time division multiplexing, the minimum spatial resolution that can be achieved is defined by the minimum width of the light pulse emitted, dispersion effects in the optical fiber cable, and the maximum frequency at which the detector operates. The pulsed light source is chosen to have a pulse width sufficiently short to provide the desired spatial resolution needed to distinguish among sites in the network. The detector is chosen to have a modulation frequency compatible with that of the pulsed light source.

Closely spaced sensor sites in a network can be distinguished, even if the pulse width of the light source is too long to allow the needed resolution, by artificially increasing the light path between sensors, for example, by introducing an additional length of optical fiber between sensor sites, without increasing the physical distance between the sensor sites. Optionally, a coil of optical fiber of known length can be inserted between any two sensors in the network.

Example 4 provides more details regarding the implementation of a TDM multiple site sensor network.

In general, light sources suitable for use in the sensor devices of this invention provide the signal or reference wavelength of interest for interrogating the transducer-analyte interaction. Sources are chosen to have characteristics suitable for use in a given device configuration, e.g., sufficient power output to obtain good signal-to-noise in a multi-site network of sensors, sufficiently short pulse width to achieve desired spatial or time resolution in a given sensor network. Light emitting diodes, laser diodes and broad band sources coupled with monochromators are suitable light sources for use in this invention.

In general, detectors are selected based on the optical property to be measured, on the wavelength region of interest for signal or reference light detection and on the desired signal sensitivity. Detectors, e.g., photodetectors, of light intensity are preferred. Detectors are chosen to have characteristics suitable for use in a given device configuration with given light sources to achieve a desired signal sensitivity and response time. PIN photodiodes and avalanche photodiodes can be employed in sensor configurations of this invention.

Optical fibers and optical fiber couplers are employed in the device configurations of this invention. Silica fiber optics (fibers and couplers) are preferred to plastic fiber optics to minimize losses.

Those of ordinary skill in the art in view of what is well-known in the art and the teachings herein, understand and appreciate the requirements for the components of single-site and multiple-site sensor devices and can select appropriate components for these devices without undue experimentation.

Transducer Molecules

Xanthene and triphenylmethane dyes were chosen as transducer molecules for sensing basic gases in the present invention because these molecules were found not only to reversibly bind basic species such as hydrazine, but also to exhibit a large change in color when bound to the analyte.

Basic gases are believed to interact with triphenylmethane dyes as illustrated below for hydrazine:

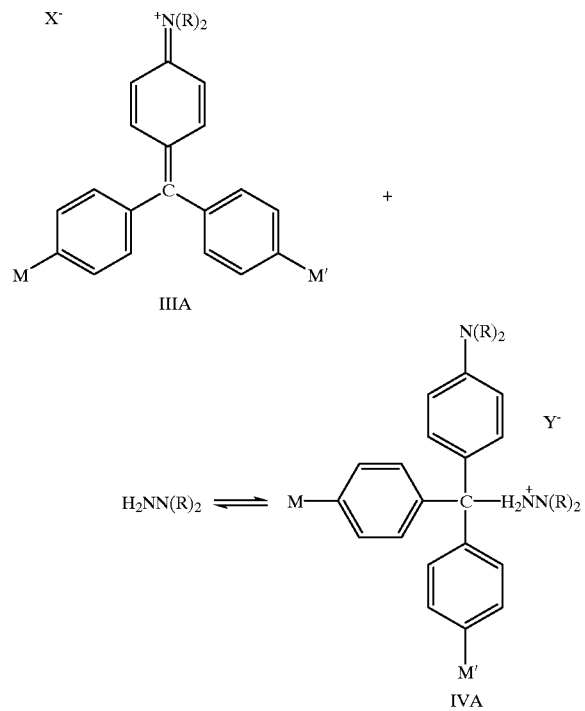

The adduct IVA is a colorless compound (A. T. Vartanyan (1961) Russ. J. Phys. Chem. 35(10):1105), so the dye IIIA is bleached on interaction with hydrazine or other basic gases. For triphenylmethane dyes having acidic hydrogens, such as aurin, a second reaction with basic gases can occur (A. T. Vartanyan (1962) Russ. J. Phys. Chem. 36(10):1142) as illustrated for aurin reacting with hydrazine:

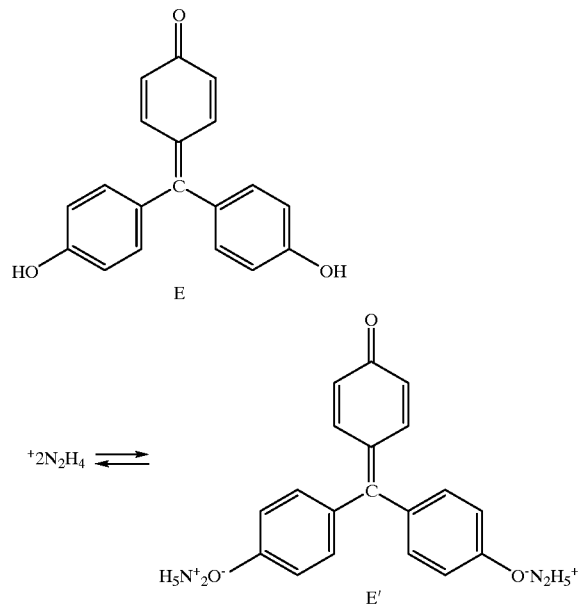

In this case the acid-base reaction results in a colored adduct (E'), with a different color spectrum than the starting dye (E).

Similar reversible reactions between basic gases and xanthene dyes can occur (A. T. Vartanyan (1962) Russ. J. Phys. Chem. 36(9):1021).

Several different classes of aromatic basic dyes are particularly useful for detection of hydrazine in the fiber optic sensor of this invention: xanthene dyes and triphenylmethane dyes. Xanthene dyes include those having the general formulas IIA and IIB:

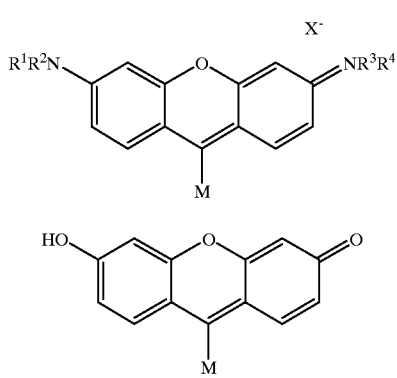

where M and each $R^1$–$R^4$ substituent, independent of one another, can be H, an alkyl group, an alkylaryl group, an aryl group or a substituted alkyl, alkylaryl or aryl group and $X^-$ is an anion.

Xanthene dyes include acridine dyes (e.g., acridine red, formula IIA where $R^1$ and $R^3$ are H, $R^2$ and $R^4$ are methyl groups, and M is H); pyronin dyes (pyronin G, formula IIA where $R^1$, $R^2$, $R^3$ and $R^4$ are all methyl groups and M is H); rhodamine and sulforhodamine dyes (rhodamine G, formula IIA where $R^1$, $R^2$, $R^3$ and $R^4$ are all ethyl groups and M is a phenyl group with an ortho-COOH group)(sulforhodamine B, an anionic xanthene dye of formula IIA where $R^1$, $R^2$, $R^3$ and $R^4$ are all ethyl groups and M is a phenyl group with an ortho and a para $SO_3^-$ group) and fluorescein dyes (e.g., fluorescein (G, below), formula IIB where M is a phenyl group with an ortho-COOH group).

Cationic, anionic and neutral xanthene dyes can be used for the detection of basic analytes, including hydrazine and hydrazine derivatives, for example, alkyl hydrazines and aryl hydrazines. Xanthene dyes of formula IIA without acid or ester groups on the M substituent are the more preferred xanthenes for use in fiber optic sensors of this invention.

Substituted xanthene dyes are also suitable for use in the sensors of this invention. Useful substituted dyes include those with alkyl group, halogen, nitro and cyano group substitution at various ring positions in formula IIA or IIB (ring numbering as labelled). Preferred subtituents are halogens, particularly fluorines and chlorines, and small alkyl groups (i.e., those having 1 to 6 carbon atoms), particularly methyl and ethyl groups. In general, any of the hydrogens of any of the rings can be replaced with a substituent. Useful substituted xanthene dyes are those in which the substituent or substituents do not significantly affect reversibility of the interaction with hydrazine or its congeners monomethylhydrazine and 1,1'-dimethylhydrazine.

Triphenylmethane dyes useful in sensors of this invention include anionic, cationic and neutral triphenylmethane dyes. Cationic triphenylmethane dyes are exemplified by crystal violet and malachite green. Anionic triphenylmethane dyes are exemplified by the generic formula D and particularly by acid violet (D, where $R=C_2H_5$ and $Y^+=Na^+$). Neutral triphenylmethane dyes are exemplified by aurin (E).

Cationic triphenylmethane dyes of general formula IIIA:

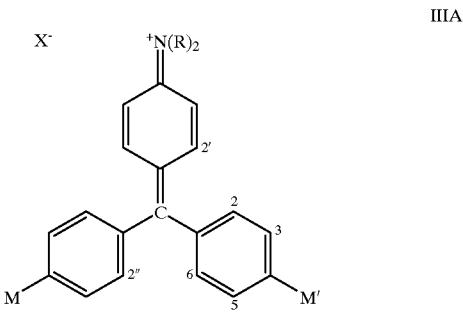

where M and M' can be H or an $N(R)_2$ group, where each R independently of all other R can be H, alkyl groups or aryl groups or alkylaryl groups or substituted alkyl, aryl or alkylaryl groups are suitable for use in this invention and those dyes in which R is H or a small alkyl group having from 1–6 carbon atoms are preferred for use in this invention. The R substituents at a given position can be the same or different. The anion $X^-$ can be any anion, but in particular, can be a halide (particularly $Cl^-$), acetate, oxalate, or $S_3^-$. Triphenylmethane dyes can also be isolated as metal halide double salts, e.g., the zinc chloride double salt of malachite green.

Anionic triphenylmethane dyes include those of formula IIIA having two or more anionic substituents (e.g., $SO_3^-$) with appropriate counterions $C^+$ (e.g., $Na^+$, $K^+$, and the like) on one or more of the aromatic rings.

Neutral triphenylmethane dyes of general formula IIIB:

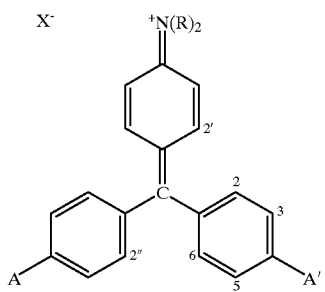

IIIB where at least one of A or A', independent of the other, is an OH or COOH and the other of A or A' can be H, OH, COOH, alkyl, aryl, alkylaryl or substituted alkyl, aryl or alkylaryl are useful in sensors of this invention.

Substituted triphenylmethane dyes are also suitable for use in the sensors of this invention. Useful substituted dyes include those with alkyl group, halogen, nitro and cyano group substitution at various ring positions in formula IIIA or IIIB (ring numbering as labelled). Preferred subtituents are halogens, particularly fluorines and chlorines, and small alkyl groups (i.e., those having 1 to 6 carbon atoms), particularly methyl and ethyl groups. In general, any of the (12 or 13) hydrogens of any of the rings can be replaced with a substituent. Useful substituted triphenylmethane dyes are those in which the substituent or substituents do not significantly affect reversibility of the interaction with hydrazine or its congeners monomethylhydrazine and 1,1'-dimethylhydrazine.

Basic dyes, including xanthene dyes and triphenylmethane dyes, were initially assessed for use in sensor application of this invention by thermal deposition of the dye on a glass slide. The optical response of the slide-deposited dye layer to hydrazine vapor (100 ppb) was measured in the wavelength range 600–800 nm in absorption mode. A cationic triphenylmethane dye (crystal violet A), a neutral triphenylmethane dye (aurin, E), and xanthene dyes (rhodamine B, F) and fluorescein (G) were initially assessed for optical response (i.e., color change and/or bleaching) to 100 ppb hydrazine. Under the initial assay conditions employed, crystal violet, the triphenylmethane dye, was found to have the most sensitive response to hydrazine. The anionic triphenylmethane dye, malachite green (B), was also found to be very sensitive to hydrazine (as well as to substituted hydrazines) when immobilized on a fiber optic sensor. Triphenylmethane dyes, closely related to crystal violet and malachite green, ethyl violet (A'), brilliant green (B'), methyl violet (C) are also suitable for use in this invention.

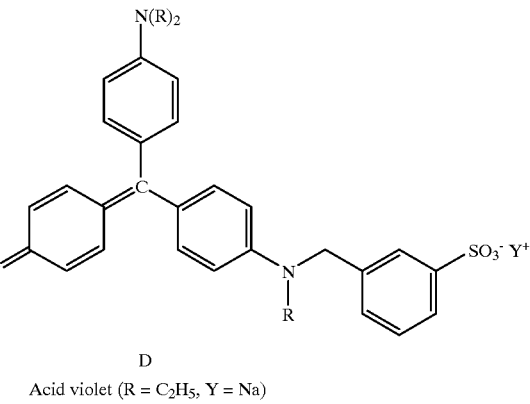

D
Acid violet (R = $C_2H_5$, Y = Na)

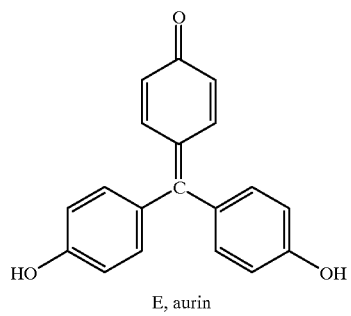

E, aurin

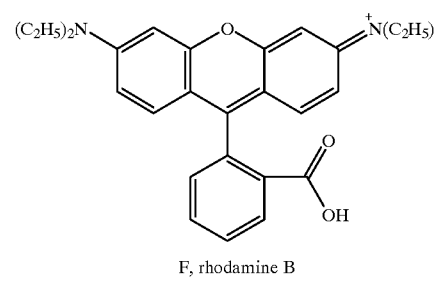

F, rhodamine B

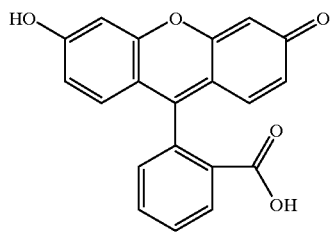

G, fluorescein

The sensor 10, as exemplified in FIG. 1A–B, consists of a xanthene or triphenylmethane dye (or mixture of such dyes) immobilized onto a fiber optic core surface. Basic gases for detection include hydrazine, alkyl hydrazines such as monomethylhydrazine and unsymmetrical dimethylhydrazine, aryl hydrazines, ammonia and alkyl amines, such as methylamine and ethylamine. The invention also includes the optoelectronic components to deliver light to the sensor and receive light signals from the sensor.

Color change as a function of interaction with an analyte is the basis of the sensing mechanism of the present invention. The present invention utilizes certain dye molecules that act as transducer molecules. The dye is immobilized or coated onto the outer surface of an optical fiber. On interaction between the analyte and the dye, a color change occurs in the immobilized or coated layer. An optical property of the light introduced into the optical fiber, where it is subject to total internal reflection, is affected in a measurable way by the color change in the fiber optic surface layer, for example by decreased or enhanced absorption at a given wavelength or wavelengths. The reaction of the dye with the analyte is preferably reversible so that the dye returns to its original color on removal of the analyte. A change of color includes bleaching of the dye.

In order to have a stable sensor, the transducer molecule must be immobilized onto the fiber surface. Methods of immobilization applicable to the use of dyes in the present invention include vacuum thermal evaporation, coating from solution, immobilization within a polymer, such as polyvinyl chloride (PVC), and covalent attachment via silane linkages between the dye and the silica fiber optic surface. The latter two methods are preferable in that the transducer molecule is coated in a repeatable manner and they yield more homogeneous coatings.

A useful sensor must have adequate sensitivity for the analyte. For example, recently proposed regulations for hydrazine and alkyl hydrazines will require detection down to levels of 10 ppb. High sensitivity can be obtained by utilizing more intense light sources and more sensitive detectors, but this approach also significantly increases both the cost of the device and power consumption. The optical properties of the transducer molecule itself can be selected to obtain high sensitivity. For example, by choosing a dye with a wavelength of maximum absorption, $\lambda_{max}$, that is close to the maximum wavelength of the light source, higher sensitivities can be achieved.

The term immobilization is broadly used herein to refer to means for providing and preferably stably maintaining dye molecules at or near the surface of a fiber optic. Dye molecules can be immobilized on the fiber surface by deposition to form a surface layer, i.e., via vapor deposition or solvent deposition. Alternatively, dye molecules can be introduced into a layer of polymer coated onto the fiber optic surface. Dye molecules can also be covalently attached to the fiber optic surface through linker groups.

A variety of methods for covalent linkage of a dye molecule to the fiber optic surface are available in the art. Dyes can be covalently attached to the surface of silica fiber optics. The dye can, for example, be coupled to the surface via a linking group or synthesized in situ on the surface.

One strategy for covalent attachment involves derivatization of the dye with an appropriate reactive coupling group which can be reacted with a previously derivatized silica fiber to form a covalent linkage to the fiber. The fiber surface can be derivatized with a silane coupling agent. The use of silane coupling agents for modifying silica surfaces is well known (See, for example, E. Pluddemann (1982) "Silane Coupling Agents" Plenum Press, New York, N.Y.) and general techniques currently used in the art can be employed to derivatize the silica fiber surface. For example, a coupling reagent such as 3-glycidoxypropyltrimethoxysilane (about a 10% V/V solution in distilled water) can be used to derivatize the fiber surface, as illustrated in Scheme 1. The bare, clean fiber surface is treated with the coupling agent solution, the solution containing the fiber is made acidic (pH 3) with 6M HCl and then heated (e.g., 75° C. for 2 h). Derivatized fibers are washed thoroughly in distilled water and dried in air with heating (e.g., 1150° C. for 4 h). As illustrated in Scheme 1 for malachite green, an amine substituted dye derivative is prepared, for example an $NH_2$ group can be introduced onto one of the phenyl rings in a triphenylmethane dye, for example, a para-substituted amino group can be introduced onto the unsubstituted ring in malachite green. Standard synthetic methods can be used for the preparation of appropriate derivatized dyes. Derivatized fibers are refluxed in a saturated solution of the derivatized dye in water to provide the covalent link of the dye. The fibers are then washed thoroughly with water and dried in air.

Scheme 2 illustrates an alternative method for covalent coupling of a dye to the silica fiber surface, i.e., in situ synthesis of the dye. 3-aminopropyltriethoxysilane can, for example, be used to derivatize the silica fiber surface. The surface amino group is initially reacted with an aromatic dialdehyde resulting in a free aldehyde on the surface. Standard methods of synthesis of triphenylmethane dyes (K. Venkataraman (1952) "The Chemistry of Synthetic Dyes" Vol. II, Chapter XXIII, Academic Press, New York, N.Y. and N. R. Ayyanger and B. D. Tilak (1971) in "The Chemistry of Synthetic Dyes" Vol. IV (K. Venkataraman, ed.) Chapter III Academic Press, New York N.Y.) can be employed to prepare the dye coupled to the silica surface. These methods are modified to use non-aqueous solution to minimize hydrolysis of surface bound materials.

In the illustrated coupling, the silica fiber surface is first derivatized using an aqueous solution (e.g., 10% V/V) of the coupling agent. The fiber is introduced into the coupling agent solution, the solution is acidified (pH 3) and heated (e.g., 75° C. for 2 h). The derivatized silica fiber is washed with water and dried in air with heating (e.g., 115° C. for 4 h). The dialdehyde (terepthalaldehyde, in Scheme 2) is condensed with the amine-functionalized silica by contacting the silica with an ethanolic solution of the aldehyde for several hours. This procedure is analogous to methods used to condense glutaraldehyde with amine-functionalized silica (H. H. Weetall (1976) Meth. Enzym. 44:134). The free aldehyde group now on the silica surface is reacted with 2 equivalents of an aromatic amine to produce the triphenylmethane dye covalently linked to the fiber surface. For example, a solution of $CuSO_4$, NaCl, and dimethylaniline all in ethanol can be added to the derivatized fiber, refluxed, if necessary, for several hours and then cooled.

The preferred method of dye immobilization for this invention is incorporation of dye molecules in an inert polymer layer in contact with the outer surface of the optical fiber core. The polymer is preferably chemically inert to the analyte and should not interact with the analyte. The polymer material does not chemically interfere with the chemical interaction of the analyte with the dye. Further, the polymer layer should be sufficiently permeable to the analyte to allow it to penetrate the layer to interact with the dye. It is also preferred that adsorption of the analyte into the polymer layer is reversible to provide for rapid response to changes in analyte concentration. The polymer itself or on exposure to the analyte should not optically interfere with the detection of the change in optical response due to the interaction of the dye with the analyte.

Linear and branched hydrocarbon polymers and their halogenated derivatives are generally useful as polymer layers of the sensors of this invention. Polyvinyl chloride (PVC) and polyisobutylene (PIB) have been found to be particularly suitable for use with triphenylmethane dyes in preparing dye-containing polymer layers for the sensors of this invention. PVC is the more preferred of these materials. In general, a broad range of polymer molecular weights can be employed so long as sufficient permeability of the layer to analyte is retained. The use of PVC's of molecular weight such that the inherent viscosity of the PVC is less than or equal to about 1 (see ALDRICH (Trademark) Catalog 1994, Aldrich Chemical Company).

To obtain good sensitivity to the analyte, the polymer layer should be plasticized. It has been found that the chemical type and the amount of plasticizer included in the polymer layer can affect sensitivity of the sensor to the analyte. In general, the type and amount of plasticizer needed to achieve good sensitivity depends on the type of polymer material used. For a given polymer material, the type and amount of plasticizer, are selected for compatibility to the polymer as is known in the art and in view of the examples herein and adjusted by routine optimization to maximize optical response to the analyte.

It has also been found that sensitivity to a given analyte (basic gas) depends upon the type and concentration of the transducer dye employed in a polymer layer. In general, the type and concentration of dye used in a given sensor application can be selected for compatibility with a given analyte and a given application, in view of the examples herein and general principles known in the art, and adjusted by routine optimization, as exemplified herein, to maximize optical response to the analyte.

The sensor systems herein have been described in their application to gaseous basic analytes; however, these sensors, devices and sensor network can be readily adapted for use in detection of basic analytes in solution or mixed media.

The following examples are provided to illustrate the invention.

EXAMPLES

Example 1

Fiber Optic Sensor having Hydrazine-Sensitive Dye as Vapor-Deposited Layer

Silica optical fibers (1000 μm in diameter) were obtained commercially (General Fiber Optics, Fairfield, N.J.). As purchased, the fibers were clad in an outer buffer layer and an inner polysiloxane-hexafluorine copolymer. Before use, the outer layer was removed mechanically and the inner layer was removed using a commercially available solvent (Dynasolve 210) and then rinsed with distilled water and dried.

In this example, the dye used was crystal violet (Structure A) which was obtained commercially (Baker Analyzed Reagent, Phillipsburg, N.J.) and used without further purification. The fiber was coated by thermal evaporation using an Edwards E306A Coatings System (Wilmington, Mass.). Dye powder was loaded into a covered molybdenum evaporation boat. After the fiber was positioned above the evaporation source, the chamber was pumped down to $5\times10^{-5}$ Torr. Evaporation proceeded by resistively heating the boat with power typical applied to the boat in the range of 500–600 W. The dye was evaporated onto the substrate for 30 s. This procedure resulted in thin, uniform, partially transparent films, the color of which was dependent on the specific dye employed. The wavelength of maximum intensity ($\lambda_{max}$) for crystal violet was 590 nm. Typical coated fiber lengths were about 2 cm.

Figure 5:
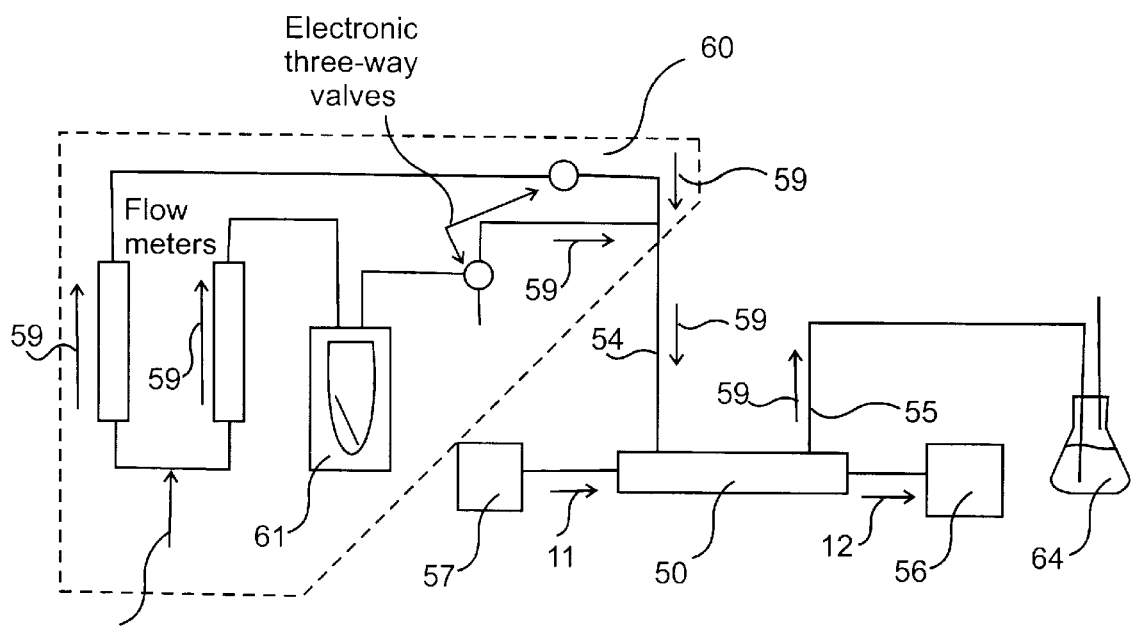
FIG. 5 is a schematic drawing of a test system for assessing sensors of this invention.

The dye-coated fiber was inserted into the sample chamber of a test sensor system, which is schematically illustrated in FIG. 5. The test sensor system contained a fiber optic test chamber 50 consisting of a "TEFLON" (Trademark) tube which was used to provide an air-tight seal and mechanical rigidity. The dye-coated optical fiber was inserted through the tube and through plastic septums held in "TEFLON" tee joints at either end of the tube. The other arms of these joints served as the input 54 and output 55 for the sample gas stream (gas flow 59) to the chamber. The output light of the optical fiber sensor was coupled directly to a monochromator and a photodetector (detector, 56) using SMA connectors external to the chamber. The light source 57 used was a commercially available laser diode operating at 635 nm with a maximum power output of 3mW (Model SPMT 03-635-3, Power Technology, Inc.). In some cases, the narrow wavelength source was replaced with a tungsten-halogen lamp with a grating monochromator. Another alternative light source examined was a light emitting diode (LED) operating at 660 nm and 2000 mcd (Archer, Forth Worth, Tex.) The output of the laser diode, LED or other source was coupled directly to the optical fiber sensor using SMA connectors.

To detect the signal, a PIN photodetector was used (Sharp, 500 series). The output from this photodetector was fed into an amplification circuit consisting of a transimpedance amplifier which converts the photodetector current to voltage and a zeroing amplifier which permits shifting of the baseline. The output from this circuit was sent to an analog-to-digital converter (Real-Time Devices, AD510) in a computer. Data (optical response in mV vs. time) were captured using in-house software, which allowed real-time graphical monitoring of the sensor response as well as data storage.

A sample gas system 60 was used to provide hydrazine/air sample mixtures (or air alone) to the sample chamber. The air employed was "dry grade". Hydrazine was supplied through a commercially available permeation tube 61 (Kin-Tek Laboratories, HRT). By adjusting the temperature of the permeation tube, the hydrazine permeation rate was varied from 10–100 ng/min. Air flow rates (from air supply 62)

over the permeation tube were also varied to achieve concentrations of 10–1000 ppb hydrazine in air. Similar permeation tubes were employed for generation of monomethylhydrazine or 1,1'-dimethylhydrazine. Initial experiments for detection of ammonia were performed by injection of a desired amount of ammonia into the flow system. A permeation tube for ammonia was employed in later experiments.

The concentration of hydrazine in air in the sample gas stream was determined by passing gas exiting the sample chamber through a 0.1M $H_2SO_4$ trap 64. The concentration of hydrazine trapped in the acid was then determined using a commercially available calorimeter test kit (Hydraver 2, Hach, Loveland,Colo.). With the known exposure time and flow rate, the average sensitivity of the sensor to hydrazine could be determined. This test kit method was also used to determine concentrations of ammonia and monomethylhydrazine, but was not found practical for measurement of 1,1'-dimehtylhydrazine concentrations. An ammonium ion selective electrode (Hach) was found to respond adequately to the 1,1'-dimethylhydrazine as a hydrazinium in 0.1 M sulfuric acid. The 0.1M $H_2SO_4$ trap quantitatively trapped all hydrazines passed through the system. This was verified by negative HACH Hydraver 2 test on a second trap placed downstream in series with the first trap.

The test system of FIG. 5 can be improved by providing for removal of the sensor from the test chamber. The improved test system, allows more accurate measurement of sensor response times. Hydrazine and hydrazine derivatives introduced into the test chamber and sample system only slowly desorb from the surfaces therein. With this slow desorption of analyte, sensor response times appeared to be very slow. Removal of the sensor from the test system, however, indicates that sensors recover in about 3 min. following exposure to analyte.

The test system employed can be used to test the sensitivity and reversibility of reaction of a variety of transducer dye molecules with basic gases including hydrazine and its derivatives. This test system can also be readily adapted by providing a source of the analyte to assess the response of the dye-coated optical fiber sensors to other analytes.

Experiments performed in the test system indicate that the sensor is sensitive to hydrazine, that the response to hydrazine is reversible and that the intensity of the response correlates to the concentration of hydrazine in the sample gas stream. The level of sensitivity of this dye-coated sensor to hydrazine is about 10 ppm.

This dye-coated sensor was found to be sensitive to the presence of water vapor in the sample. It is believed that the sensor responses observed were due to water absorption onto the fiber surface rather than due to a specific interaction between the dye and water. This result suggests that absorption of water onto the fiber should be avoided.

Example 2
Fiber Optic Sensor having Hydrazine-Sensitive Dye as Vapor-Deposited Layer (Malachite Green)

Malachite green (B) was used as the transducer molecule in an optical fiber sensor analogous to that described in Example 1. The thickness of the deposited dye layer is expected to be similar to that obtained with crystal violet since care was taken to perform the thermal deposition under the same conditions. The $\lambda_{max}$ of this dye is 621 nm, which is closer to the wavelength of the light source chosen for use in the test system (635 nm) than the $\lambda_{max}$ (at 590 nm) of crystal violet.

Malachite green was prepared from commercially available malachite green carbinol hydrochloride (Aldrich Chemical Co., Milwaukee, Wis.) by hydrolysis. Specifically, malachite green carbinol hydrochloride was dissolved in water and the solvent was allowed to evaporate yielding the chloride salt as a dark solid, which was used as the transducer without additional purification.

A fiber optic sensor was prepared as in Example 1 and analogous experiments were performed in an identical test apparatus. The sensitivity of this dye-coated sensor to hydrazine is about 10 ppb (about 1,000-fold improved over the sensor of Example 1). This sensor was also demonstrated to reversibly detect monomethylhydrazine and 1,1'-dimethylhydrazine at levels in air below 100 ppb.

A sensor coated with malachite green prepared as described above was inserted into the test apparatus analogous to that described in Example 1, except that samples of ammonia in air were prepared in a "TEFLON" bag by introducing the desired amount of ammonia using a gas-tight syringe. Optical response of the sensor was measured as a function of time as the sensor was exposed sequentially to 1 ppm ammonia in air and air with no analyte. The results of this experiment indicate that the optical fiber sensor responds to ammonia and that the response is reversible. This sensor was found to be about 40 times more sensitive to hydrazine than to ammonia.

Figure 6:
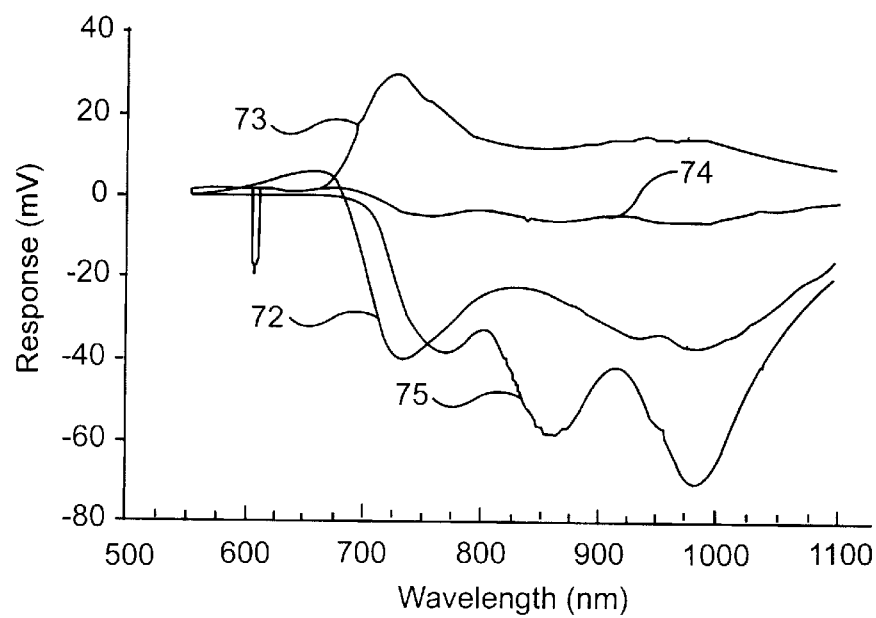
FIG. 6 is a plot of sensor response as a function of wavelength for selected concentrations of ammonia, hydrazine, monomethylhydrazine or 1,1'-dimethylhydrazine. The sensor employed is coated with malachite green as described in Example 2.

The wavelength dependence of sensor response to hydrazines and ammonia was determined using the test system of Example 1 using a tungsten-halogen lamp light source with monochromator. The intensity of the sensor response to either ammonia 72 (10 ppm), hydrazine 73 (500 ppb), monomethylhydrazine 74 (84 ppb) or 1,1'-dimethylhydrazine 75 (30 ppb) in air relative to the sensor response in air alone is plotted vs. wavelength in FIG. 6. These results indicate that hydrazine sensor measurements in the wavelength range from about 680 nm to about 740 nm, where the response to ammonia is at a minimum, would minimize interference from ammonia. The maximum differential between the response to ammonia and monomethylhydrazine occurs in the same wavelength region (about 720 nm). The maximum differential between the response to ammonia and 1,1'-dimethylhydrazine occurs further to the infrared at about 850 or 980 nm.

Example 3
Fiber Optic Sensor Having Hydrazine-Sensitive Dye (Malachite Green)Immobilized in a Thin Polymer Film An optical fiber (1000 μm diameter core silica optical fiber) was prepared for coating as in Example 1. Malachite green was immobilized along the fiber within a polymer film (e.g., a poly(vinylchloride) film) which was coated onto the bare fiber, a length of about 10 cm. A solution of low molecular weight PVC (Aldrich Chemical Co., Milwaukee, Wis.; Cat. No. 18,958-8, inherent viscosity 0.68), bis-(2ethylhexyl)sebacate plasticizer (also from Aldrich Chemical Co.) and malachite green chloride, prepared as described in the previous example, was prepared in tetrahydrofuran (THF). The weight percent composition of the solution was 27.7:70.4:1.9% PVC:plasticizer:malachite green.

The core of the fiber was coated by brief immersion in the THF coating solution. A thin solid film of PVC containing the chemically sensitive malachite green was formed on the fiber core upon evaporation of the solvent in air. The dye layer on the fiber was believed to be relatively thin, since no coloration due to the dye was observed visually on coated fibers. Subsequently, SEM studies of cross-sectioned coated fiber indicated that the polymer layer was about 5–6 μm thick.

Dye-containing polymer-film sensors have also been successfully prepared with medium molecular weight PVC (Aldrich Chemical Co., Cat. No. 43,677-2, inherent viscosity 0.92 and relative viscosity 2.23). Molecular weight of the PVC employed does not appear to significantly affect sensitivity of the sensor, however, PVC with inherent viscosity of 1 or less is presently preferred.

Sensing of basic gases with this fiber was performed in the evanescent wave mode, as in Example 1. This sensor was exposed to hydrazine in the test system described in Example 1 using the 635 nm diode laser light source and data acquisition electronics. The photodetector in this case was a Burr-Brown OPT209 PIN photodiode detector with on-chip amplifier.

Figure 7A:
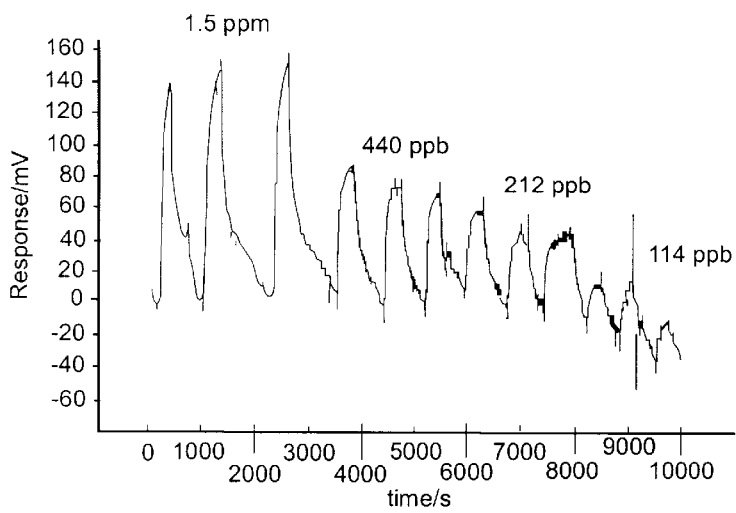
FIGS. 7A–C are plots of sensor response as a function of time (at 635/nm) to varying concentrations of hydrazine during a 10-day period of continuous operation. The sensor was periodically exposed to hydrazine at the indicated concentrations. The sensor response times in these experiments are affected (i.e., appear slower) because of adsorption (and slow desorption) of hydrazine on surfaces in the test system.
Figure 7B:
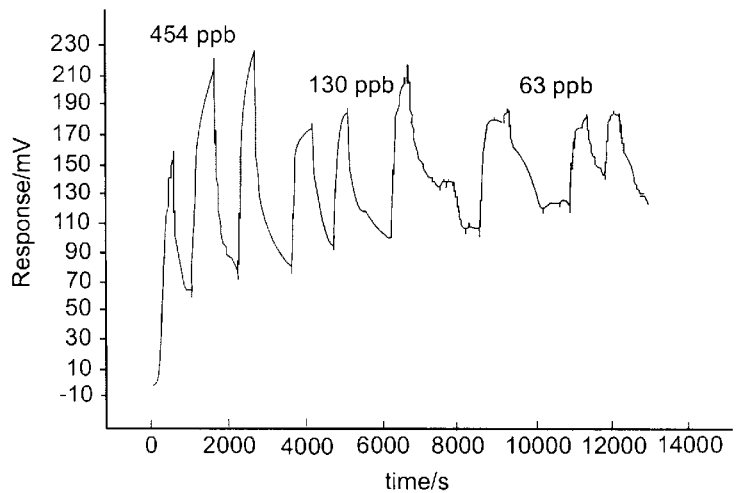
Figure 7C:
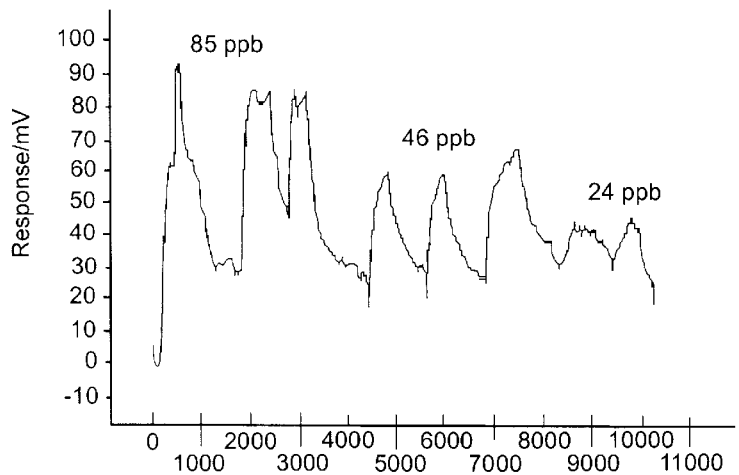
Figure 8:
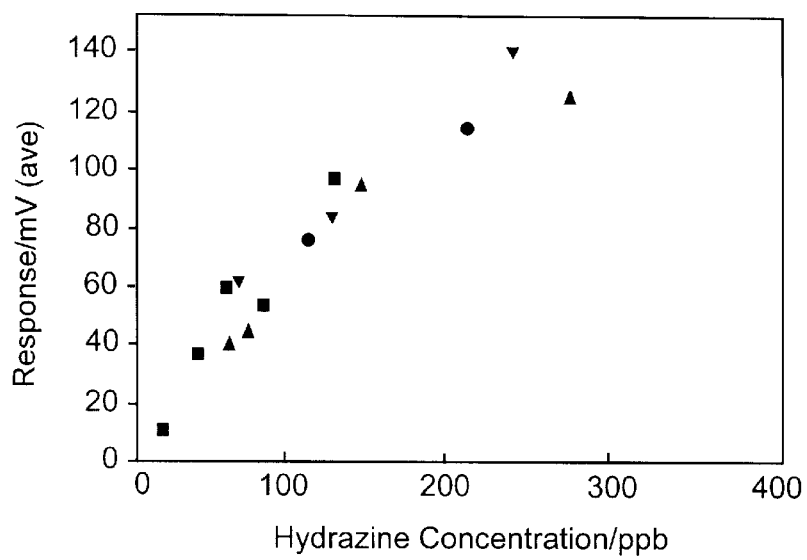
FIG. 8 is a graph of sensor response as a function of hydrazine concentration over the course of 10 days of continuous operation. Data shown are from day 2 (▼), day 3(●), day 6 (■) and day 7 (▲).

The fiber was exposed intermittently to hydrazine vapor from 5.4 ppm to 24 ppb over the course of 10 days of testing. Typical responses at 635/nm obtained during operation of the sensor are shown in FIG. 7A–C. These results indicate that fiber sensors prepared by immobilization of chemically sensitive malachite green in a polymer film respond to target analytes similarly to sensors prepared with thermally evaporated dye films. Reproducible responses were obtained with repeated exposures to hydrazine over the course of 10 days, as shown in FIG. 8.

The comparative response of a malachite green/PVC fiber sensor and a control optical fiber having an analogous PVC film without immobilized dye exposed repeatedly to 5.4 ppm hydrazine was examined. The results obtained show that the PVC film alone does not itself respond to hydrazine and that the sensor response observed is due to interaction of the analyte with the film-immobilized dye.

Early sluggish response of the sensor to hydrazine on the first day after the PVC-dye coating was applied suggests that a conditioning period (about 24–48 h) will provide for more reliable responses.

A polymer/dye film coated sensor prepared as above was exposed to monomethylhydrazine vapor and the sensor was shown to be useful for detection (and quantitation) of monomethylhydrazine. This sensor was also found to respond to ammonia vapor. The relative sensitivities of this sensor to hydrazine, monomethylhydrazine and ammonia at $\lambda$=635 nm are 20:1:0.06, respectively.

Sensitivity of the fiber optic sensor to hydrazine was found to depend upon the weight percent of malachite green in the PVC coating solution. Optimum sensitivity of about 4–5 mV/ppb ($\lambda$=635 nm) was obtained at about 0.4–0.6% weight percent (percent malachite green by weight) in the coating solution. Sensitivity increased as the weight percent of malachite green in the coating solution was increased up to the maximum and then sensitivity dropped off with further increases in weight percent dye. Sensitivity of 1.5 mV/ppb or higher was obtained for the range of weight percent of malachite green ranging from about 0.05% to about 1%. The concentration of dye in the coated film has not, however, been directly measured.

Sensor response (to 150 ppb hydrazine) was found to depend upon the weight percent of plasticizer, bis-(ethylhexyl)sebacate (BEHS), employed in the PVC coating solution. Earlier experiments had employed about 70% by weight of BEHS. Sensor response was measured at 0%, 40%, 80% and 100% of the original weight percent of BEHS used, 100% being equivalent to the original amount of BEHS used. Unplasticized films do not respond to hydrazine and hydrazine response generally increases with increasing amount of plasticizer. Response of PVC/dye film sensors to 40 ppb hydrazine increased approximately linearly from 40–80 relative weight percent plasticizer (BEHS).

PVC/malachite green film sensors were prepared using other plasticizers, including 2-nitrophenyloctylether (NPOE), bis-(2-ethylhexyl)adipate and dibutylsebacate (DBS). Coating solutions containing 29% PVC, 70.5% plasticizer and 0.5% by weight malachite green were employed to form sensor films. Sensor response to about 50 ppb hydrazine was measured. All of the plasticizers used gave acceptable responses. Sebacate plasticizers produced more reasonable responses than NPOE or the adipate and are presently preferred. BEHS provided generally better sensor response than the other plasticizers used.

Example 4:
A Multi-Site Sensor Network for Detection of Basic Gases

Data collection from individual sensors in a multiple site sensor network such as that of FIG. 4 requires some form of multiplexing. Time division multiplexing can be employed in such systems to provide the desired degree of spatial resolution.

Figure 9:
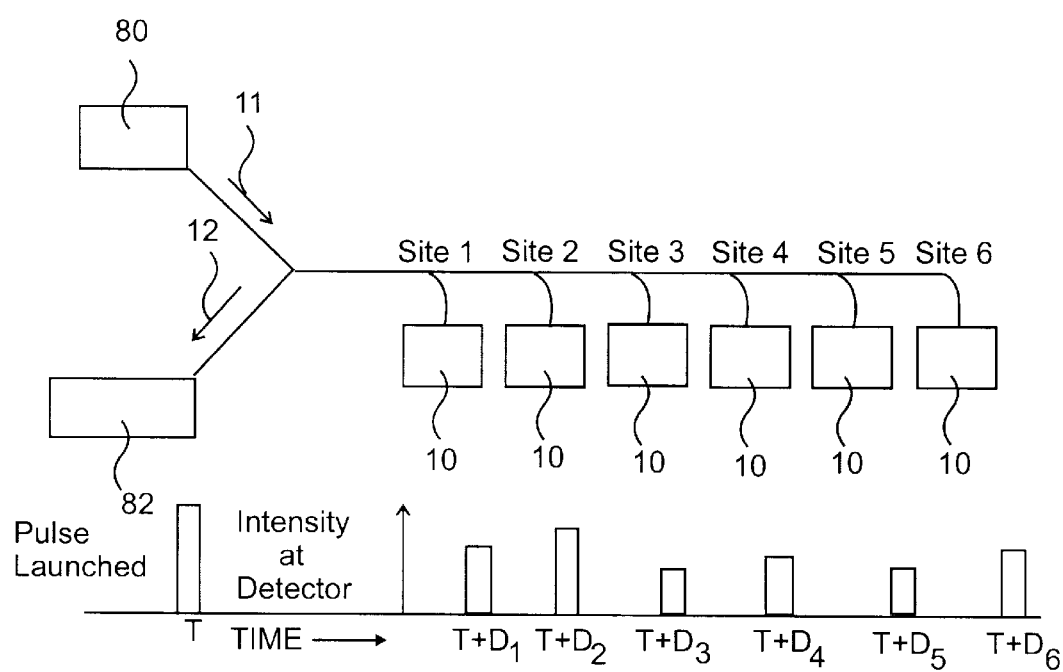
FIG. 9 is a schematic of a linear array network for use with the back reflected fiber optic geometries showing the time sequence converting the spatial domain to the time domain.

FIG. 9 is a scheme illustrating how spatial information in a linear array network is converted into the time domain using this type of multiplexing. The light source 80 is pulsed (at time T) and intensity at the detector 82 is followed as a function of time. Signal reflected back from each spatially separate sensor 10 site (Site 1–Site 6) is detected as a function of time. Signal from the site 1 (nearest to the detector) is received at $T+D_1$ (delay 1) and from subsequent more distant sites with increasing delays ($T+D_2$, $T+D_3$, ... $T+D_n$, where n is the number of spatially separated sensors in the network). In a system in which the sensors are fixed at given distances from the detector, data for a given sensor is collected in the time window for reflection of its signal through network to the detector. Like the single-site sensor system, the multiple site network can be provided with a referencing system. For example, alternating pulses of signal and reference wavelengths, respectively, can be launched into the network with subsequent detection as a function of time of signal (for all sensors sites) and reference light (for all sensor sites), respectively, exiting the network.

When a network is operated under time division multiplexing, the minimum spatial resolution that can be achieved is defined by the minimum width of the light pulse emitted, dispersion effects in the optical fiber cable and the maximum frequency at which the detector operates. To achieve a spatial resolution of 2 meters, for example, a modulation frequency of 150 MHZ (equivalent to a pulse width of 3.5 ns) and a detector cutoff frequency of at least 150 MHz is required. Detectors suitable for use in such a time division multiplexing system are readily available from commercial sources. LED's are readily commercially available and inexpensive light sources which can provide wavelengths suitable for signal and reference light sources in the sensors of this invention. LEDs that have been used in sensor systems specifically exemplified herein have pulse-widths in the range of about 25 ns which is equivalent to a spatial resolution of only 7.5 m.

To obtain spatial resolution between sensor sites in a network system of 2 meters with such LEDs, the optical path distance between the sites can be artificially increased, for example, by introducing an additional length of optical fiber, increasing the light path between the sensors (e.g., to 7.5 m), without increasing the physical distance between the sensors.

The network of FIG. 9 is a linear array network with six sensor sites. Coupling ratios indicated at junctions in the network are those needed to ensure that equal amounts of light reach each fiber optic sensor (a preferred design).

Power budget should also be considered in the design of a multiple-site fiber optic sensor network. The light intensity input into the system, the dynamic range of each individual sensor and system losses define the power budget and determine the maximum number of sites that can be incorporated within the sensor network. It is estimated that total power input required for a six sensor network is about 6 $\mu$W (about 1 $\mu$W/sensor. Estimated losses in the fiber (assuming 0.5 Km of fiber with loss of 10 dB/Km) and estimated insertion loss/coupler increase the estimated power requirement in a six site network to about 120 $\mu$W. Laser diode output is more than adequate, particularly when pulsed at a very small duty cycle, to provide the required power.

Figure 10:
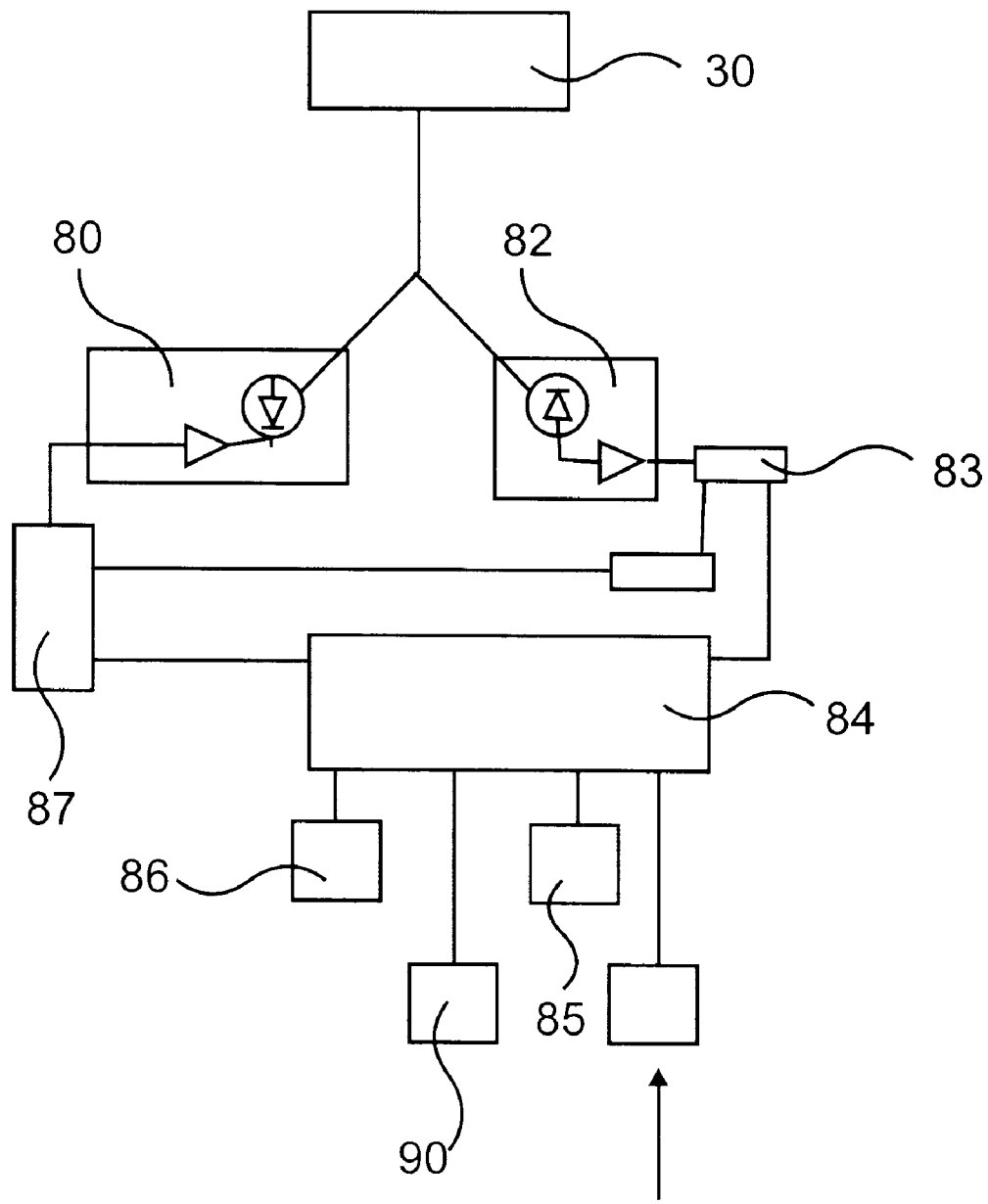
FIG. 10 is a schematic drawing of the electrooptic components and interconnectors for an exemplary multi-site fiber optic sensor network.

FIG. 10 illustrates the electrooptical components with flow chart of a time division multiplexing based fiber optic sensor network of FIG. 4. In the system of FIG. 10, the light source, LED and driver 80 and detector, avalanche photodiode 82 are optically coupled into the network of sensors 30. A high speed digitizing circuit 83 digitizes signals from the detector for further processing by microprocessor 84 connected to a serial communications interface 92 and optional printout 85 and display 86. The digitizing circuit is electronically coupled to a light source pulsing circuit 87 and microprocessor 84 and timing circuit 88. The digitizing circuit can be based upon a track-and-hold amplifier with appropriate track-to-hold settling time. In this case, a track-and-hold amplifier is provided for each individual sensor site. Once this amplifier is set to "hold" the signal, detector data are held until the end of a scan cycle. The data collected is then converted to a digital signal for example using a flash A/D system that will allow for sampling as high as 500 megasamples per second.

Timing circuit 88 can be based on a high frequency oscillator followed by a long divider chain. The base frequency of the timing circuit oscillator is chosen to provide the shortest time interval corresponding to the light propagation time for a 2-meter round trip in the network. The long divider chain, for example three decades allow selection of times from 10 to 1000 ns (equivalent to 1–999 meters of fiber length). A set of digital comparators are included to compare a preset number representing the known sensor location with the counter output, so that a time signal can be obtained at any of 999 time intervals (distances) after an initial time which is established from a reset caused to occur at any arbitrary rate off the far end of the divider chain. A cycle rate of between 10 to 100 HZ is believed suitable.

The reset pulse will be used to reset all circuits to establish the beginning of a cycle and also to trigger the laser launch pulse. As the light pulse from the laser diode travels down the optical fiber, the intensity of reflected light will be measured. It will be assumed that the location of each sensor is known and entered into the microprocessor memory by the user via a keypad 90 incorporated into the instrumentation. The microprocessor 84 then determines the time corresponding to each site and enter these numbers into the latches. The numbers entered will be compared to time after pulse launched as measured in the counter chain. As each time is reached, a hold signal, will be generated to cause a track-and-hold amplifier to hold the incoming light signal being received at that time. This signal corresponds to the light intensity and therefore to the concentration of hydrazine species at each site.

From launch pulse, total measurement time for all sites with take about 10 $\mu$s. A cycle time of 10 to 100 ms (a 10–100 Hz repetition rate) permits ample time to multiplex the incoming signals held in the track-and-hold amplifier into an analog-to-digital converter and subsequently transfer these digital signals to the microprocessor. The microprocessor makes the necessary computations, controls the display and executes other control functions. The next cycle is then started using the reference light source.

In operation, the location of sites in the network is entered and stored in the microprocessor before actual measurements are made. Using this input, the microprocessor generates timing signals that correspond to the actual distances to specific sensor sites. The timing signals are used to control individual track-and-hold amplifiers which sample the voltage generated by the photodetector corresponding to reflected light pulses exiting the network.

The pulsing detection and data analysis circuits and methods of the sensor network systems of this invention are conventional in the art and one of ordinary skill in the art can adapt a variety of such conventional techniques and procedures to data collection and analysis in such systems in view of what is known in the art and the descriptions herein.

Those of ordinary skill in the art will appreciate that components, systems and devices other than those specifically described herein can be employed and readily adapted for use in the systems and devices of this invention. Further, it will be appreciated that methods for immobilizing transducer molecules other than those specifically described herein can be employed and readily adapted for making sensors of this invention.

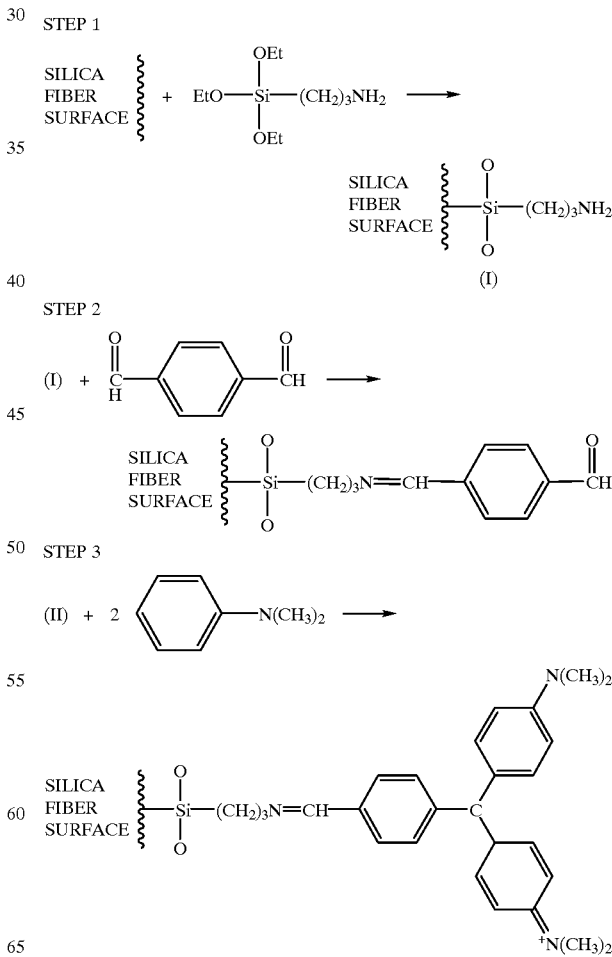

SCHEME 2

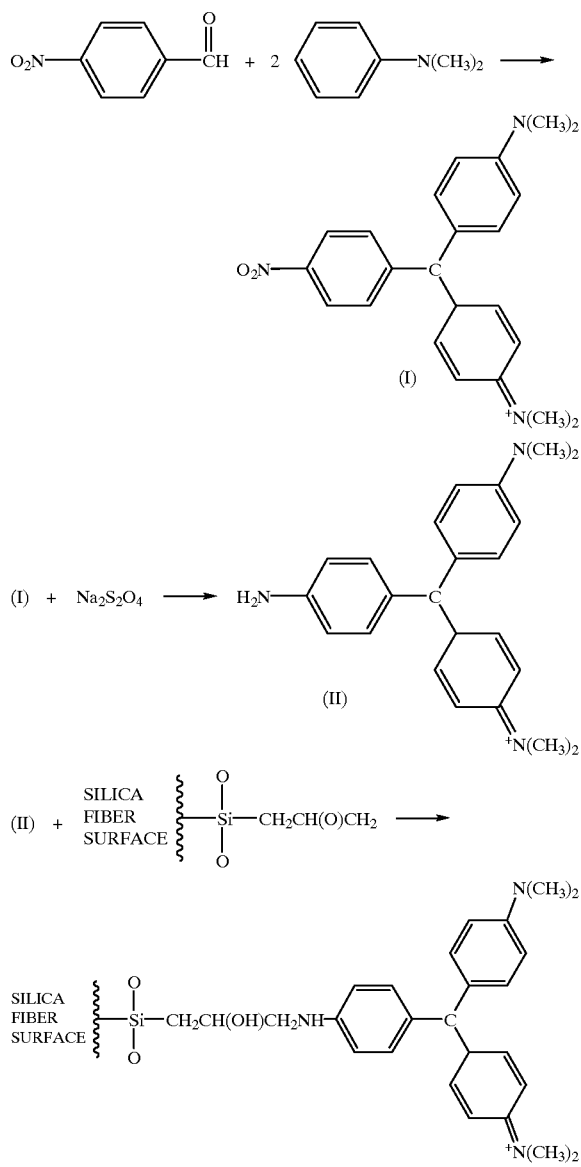

We claim:

1. A fiber optic sensor for detection of basic gases which comprises an optical fiber having a cladding and a fiber optic core and a layer comprising a dye in contact with an outer surface of said fiber optic core wherein said dye undergoes a color change on interaction with a basic gas, wherein said dye is selected from the group consisting of tripenylmethane dyes, xanthene dyes and combinations thereof and wherein said layer comprises said dye immobilized in a polymer.

2. The fiber optic sensor of claim 1 wherein said polymer is poly(vinylchloride).

3. The fiber optic sensor of claim 2 wherein said polymer layer further comprises a plasticizer.

4. The fiber optic sensor of claim 3 wherein said plasticizer is a dialkyl sebacate plasticizer.

5. The fiber optic sensor of claim 4 wherein said plasticizer is bis-(2-ethylhexyl) sebacate.

6. The fiber optic sensor of claim 1 wherein said dye is a triphenylmethane dye.

7. The fiber optic sensor of claim 6 wherein said dye is malachite green.

8. The fiber optic sensor of claim 6 wherein said dye is crystal violet.

9. A fiber optic sensor network for detection of basic gases which comprises:
   a. a plurality of optical fiber sensors of claim 1,
   b. a light source optically coupled to said sensors which provides at least one wavelength of light at which said color change can be monitored;
   c. a light detector optically coupled to said sensor for measuring optical changes in light exiting said sensor; and
   (d) means for correlating the detected optical change to the presence of basic gas.

10. The fiber optic sensor network of claim 9 wherein in each of said sensors said optical fiber has an entrance end and a distal end which is reflective and said light source and said detector are both optically coupled to the entrance ends of each said optical fibers.

11. The fiber optic sensor network of claim 9 wherein said optical sensors are positioned at different distances from said detector.

12. The fiber optic sensor network of claim 11 wherein said light source is pulsed and said light detector can monitor light intensity as a function of delay time for reflection of said pulsed light back from each of said sensors.

13. A fiber optic sensor network of claim 9 wherein the length of optical fiber between at least two sensors is greater than the physical distance between said sensors.

14. The fiber optic sensor of claim 1 wherein a portion of said cladding is removed and said layer is in contact with said exposed outer surface of said optical fiber core.

15. The fiber optic sensor of claim 1 wherein said optical fiber has an entrance end and a distal end which is reflective such that light entering said entrance end is reflected of said distal end an exits the sensor through said entrance end.

16. The fiber optic sensor of claim 15 wherein said optical fiber has an entrance end and an exit end such that light entering said entrance end exits said sensor at said exit end.

17. The fiber optic sensor of claim 1 wherein said dye is a triphenylmethane dye.

18. The fiber optic sensor of claim 17 wherein said dye is a dye of formula:

IIIA where the M and M' groups can be H or an $N(R)_2$ group and the R groups, which can be the same or different groups at different sites, can be H, an alkyl group, an aryl group or alkylaryl groups and X is an anion.

19. The fiber optic sensor of claim 18 wherein M is H, M' is $N(R)_2$ and each R group is selected, independently of other R groups, from H or small alkyl groups having from 1–6 carbon atoms.

20. The fiber optic sensor of claim 18 wherein M and M' are both an $N(R)_2$ group.

21. The fiber optic sensor of claim 18 wherein each R group, independently of any other R groups, is selected from H or small alkyl groups having from 1–6 carbon atoms.

22. The fiber optic sensor of claim 17 wherein said dye is selected from the group consisting of crystal violet, malachite green, brilliant green, methyl violet and ethyl violet.

23. A method for detection of a basic gas analyte which comprises contacting the fiber optic sensor of claim 1 with an environment that may contain said basic gas and thereafter measuring the optical response of the sensor on interaction with said environment.

24. The method of claim 23 wherein the basic gas is a hydrazine or alkyl hydrazine.

25. The method of claim 23 wherein the basic gas is ammonia or an amine.

26. The method of claim 23 wherein the basic gas is selected from the group consisting of hydrazine, monomethylhydrazine and 1,1'-dimethylhydrazine.

27. The method of claim 23 wherein the basic gas is detected in the presence of ammonia, hydrogen sulfide, $SO_2$ or water.

28. A fiber optic sensor device for detection of basic gases which comprises:
  (a) an optical fiber sensor of claim 1,
  (b) a light source optically coupled to said sensor which provides at least one wavelength of light at which said color change can be monitored;
  (c) a light detector optically coupled to said sensor for measuring optical changes in light exiting said sensor and
  (d) means for correlating the detected optical change to the presence of basic gas.

29. The fiber optic sensor device as in claim 28 wherein a portion of the cladding of said optical fiber is removed to expose an outer surface of said core.

30. The fiber optic sensor device of claim 28 wherein said optical fiber has an entrance end and a distal end which is reflective and said light source and said detector are both optically coupled to the entrance end of said optical fiber.

31. The fiber optic sensor device of claim 28 wherein said optical fiber has an entrance end and an exit end, said light source is optically coupled to said entrance end and said detector is optically coupled to said exit end.

32. The fiber optic sensor device of claim 28 wherein said light source further provides a second wavelength of light that is substantially unaffected by the color change of said dye and can be used as a reference.

33. The fiber optic sensor device of claim 28 which comprises two light sources: a signal light source which provides a wavelength of light at which said color change can be monitored and a reference light source which provides a wavelength of light substantially unaffected by the color change of said dye.

34. The fiber optic sensor device of claim 28 wherein the intensity of said signal light source and said reference light source can be separately controlled.

35. The fiber optic sensor device of claim 28 wherein said light source can provide light pulses.

36. The fiber optic sensor device of claim 28 wherein the dye is immobilized in poly(vinylchloride).

37. The fiber optic sensor device of claim 36 where the poly(vinylchloride) layer comprises a dialkyl sebacate plasticizer.

38. A method for detection of a basic gas analyte which comprises the steps of:
  (a) contacting a fiber optic sensor with an environment that may contain a basic gas where the sensor comprises an optical fiber having a cladding, a fiber optic core and a layer comprising a triphenylmethane dye or combination of triphenylmethane dyes which undergo a color change on interaction with said basic gas wherein the dye has the formula:

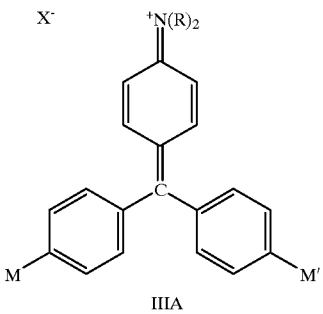

IIIA where M and M' groups are selected from the group consisting of H and $N(R)_2$ groups where the R group, which can be the same or different groups at different sites are selected from the group consisting of H, an alkyl group, an aryl group and an alkyl aryl group and $X^-$ is an anion;
  (b) measuring the optical response of the sensor on interaction with said environment; and
  (c) correlating the optical response to the presence of basic gas in the environment.

39. The method of claim 38 wherein the basic gas is hydrazine or an alkyl hydrazine.

40. The method of claim 39 wherein hydrazine or an alkyl hydrazine is detected in the presence of ammonia, hydrogen sulfide, $SO_2$ or water.

41. The method of claim 38 wherein the basic gas in ammonia or an amine.

42. A method for detection of a basic gas analyte which comprises the step of
  (a) contacting a fiber optic sensor with an environment that may contain a basic gas where the sensor comprises an optical fiber having a cladding, a fiber optic core and a layer comprising a xanthene dye or combination of xanthene dyes which undergo a color change on interaction with said basic gas wherein the dye has the formula:

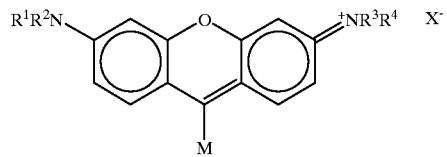

where M and each $R^1$–$R^4$, independently of one another, are selected from the group consisting of H, an alkyl group, an alkylaryl group and an aryl group and wherein $X^-$ is an anion; and
  (b) measuring the optical response of the sensor on interaction with said environment.

43. The method of claim 42 wherein the basic gas is hydrazine or an alkyl hydrazine.

44. The method of claim 42 wherein the basic gas is ammonia or an amine.

* * * * *

UNITED STATES PATENT AND TRADEMARK OFFICE
CERTIFICATE OF CORRECTION

PATENT NO. : 6,328,932 B1
DATED : December 11, 2001
INVENTOR(S) : Carter et al.

It is certified that error appears in the above-identified patent and that said Letters Patent is hereby corrected as shown below:

Column 23,
Line 55, please delete "tripenylmethane" and replace it with -- triphenylmethane --.

Column 24,
Line 42, please delete "claim 1" and replace it with -- claim 14 --.

Signed and Sealed this

Twenty-fourth Day of September, 2002

Attest:

JAMES E. ROGAN
Attesting Officer     Director of the United States Patent and Trademark Office